United States Patent [19]

Akers

[11] Patent Number: 5,607,550
[45] Date of Patent: Mar. 4, 1997

[54] ABSORBENT NONWOVEN FABRIC AND ITS PRODUCTION

[75] Inventor: Paul J. Akers, Coventry, United Kingdom

[73] Assignee: Courtaulds Fibres (Holdings) Limited, United Kingdom

[21] Appl. No.: 381,834

[22] PCT Filed: Aug. 11, 1993

[86] PCT No.: PCT/GB93/01708

§ 371 Date: Feb. 7, 1995

§ 102(e) Date: Feb. 7, 1995

[87] PCT Pub. No.: WO94/04751

PCT Pub. Date: Mar. 3, 1994

[30] Foreign Application Priority Data

Aug. 13, 1992 [GB] United Kingdom ............. 9217222

[51] Int. Cl.⁶ ............................................. D21H 13/12
[52] U.S. Cl. .................... 162/102; 162/146; 162/157.4
[58] Field of Search ................................. 162/102, 146, 162/157.4, 9, 157.1, 157.2, 157.3, 157.6, 157.7

[56] References Cited

U.S. PATENT DOCUMENTS

| | | | |
|---|---|---|---|
| 3,826,711 | 7/1974 | Scitoggen et al. | 162/146 |
| 4,552,618 | 11/1985 | Kopolow | 162/146 |
| 4,654,039 | 3/1987 | Brandt et al. | 604/368 |
| 4,655,877 | 4/1987 | Horimoto et al. | 162/146 |
| 4,808,266 | 2/1989 | Faurie | 162/157.6 |
| 4,986,882 | 1/1991 | Mackey et al. | 162/146 |
| 5,147,343 | 9/1992 | Kellenberger | 604/368 |

FOREIGN PATENT DOCUMENTS

| | | |
|---|---|---|
| 0257951 | 3/1988 | European Pat. Off. . |
| 0273075 | 7/1988 | European Pat. Off. . |
| 0339461 | 11/1989 | European Pat. Off. . |
| 0359615 | 3/1990 | European Pat. Off. . |
| 0414541 | 2/1991 | European Pat. Off. . |
| 0437816 | 7/1991 | European Pat. Off. . |

*Primary Examiner*—Peter Chin
*Attorney, Agent, or Firm*—Howson and Howson

[57] ABSTRACT

A wet-laid nonwoven fabric comprises a blend of 1 to 50% by weight of fibres of a water-swellable water-insoluble superabsorbent polymer and 99 to 50% by weight of less absorbent fibres, for example fibres having an absorbency of less than 10 g/g measured by retention to centrifuging of a 0.9% by weight saline solution.

12 Claims, No Drawings

ABSORBENT NONWOVEN FABRIC AND ITS PRODUCTION

TECHNICAL FIELD

This invention relates to a wet-laid nonwoven fabric useful in absorbent products such as diapers, incontinence pads, sanitary napkins and tampons and in wiping materials for mopping up spills of aqueous fluids. A wet-laid nonwoven fabric is a fabric comprising fibres which have been deposited from an aqueous suspension of fibres.

BACKGROUND ART

EP-A-437816 discloses a nonwoven wet-laid superabsorbent material produced by the process of blending superabsorbent polymer particles with a liquid to form a slurry, mixing fibres with that slurry, filtering that slurry/fibre mixture to remove a portion of the liquid and drying the superabsorbent slurry/fibre mixture to form a nonwoven wet-laid superabsorbent material.

EP-A-359615 discloses a method for the manufacture of a superabsorbent fibrous structure in which a dry solid absorbent is applied directly to a wet-laid web of cellulosic fibres prior to drying the wet web.

EP-A-273075 discloses a high water-absorbency paper made by sheeting a mixture of wood pulp fibre, water-soluble resin and high water-absorbency resin.

Absorbent products such as diapers which include particles of a superabsorbent polymer such as crosslinked sodium polyacrylate disposed between layers of wood pulp are known for example from EP-A-257951.

DISCLOSURE OF INVENTION

A wet-laid nonwoven fabric according to the invention comprises a blend of 1 to 50% by weight of fibres of a water-swellable water-insoluble superabsorbent polymer and 99 to 50% by weight of less absorbent fibres, for example fibres having an absorbency of less than 10 g/g measured by retention to centrifuging of a 0.9% by weight saline solution.

In a process according to the invention for the production of a wet-laid nonwoven fabric, fibres of a water-swellable water-insoluble superabsorbent polymer and less absorbent fibres, for example fibres having an absorbency of less than 10 g/g as measured above, are slurried together in water, the slurry is deposited as a layer on a foraminous support so that part of the water drains from the layer of slurry on the support, and the resulting fibrous layer is dried to form the nonwoven fabric.

The use of fibres of the water-swellable water-insoluble superabsorbent polymer, rather than the same polymer in particulate form, has significant advantages in many respects. The superabsorbent polymer fibres are more securely retained both during formation of the wet-laid nonwoven fabric and when the fabric is in use as an absorbent product. Uniform dispersion of the superabsorbent polymer is facilitated. The superabsorbent polymer fibres become part of the fibrous structure of the nonwoven fabric and contribute towards its cohesive strength, whereas the presence of superabsorbent polymer particles reduces the strength of the nonwoven fabric.

The absorbency of fibres can be measured by the free swell test, in which 0.5 g fibre is dispersed in 30 ml aqueous liquid and left for 5 minutes. The aqueous liquid used is generally 0.9% by weight saline solution, which is generally absorbed to a extent similar to body fluids such as urine. The test can alternatively be carried out with either tap water or demineralised water. For all absorbency measurements, the fibre is conditioned at 65% relative humidity and 20° C. before being tested. The dispersion is then filtered through a sintered Mark 1 funnel of pore size 100–160 microns and is left for 5 minutes or until it stops dripping, whichever is the longer. The amount of aqueous liquid filtered through the funnel is weighed and the weight of aqueous liquid absorbed by the fibres is calculated by subtraction. A superabsorbent polymer is one having an absorbency of at least 20 g/g in the free swell absorbency test using 0.9% by weight saline solution. Usually, superabsorbent polymers have an absorbency in the range 30–60 g/g in this test.

In addition to the above test, the retention by the fibre or filament of the aqueous liquid (such as saline solution) after application of pressure can be measured in a retention test by weighing the aqueous liquid expressed after application of pressure at about 3.4 kPa for 5 minutes or until dripping stops, whichever is the longer. Superabsorbent fibre usually has an absorbency of at least 20 g/g in this retention under load test.

In an alternative retention test, the retention to centrifuging is measured by rotating swollen fibre in a centrifuge having 25 mm-diameter 75 mm-long tubes with a coarse stainless steel mesh base fitted with a type AG/F glass microfibre filter disc. The diameter of the spinning assembly is 25 cm. The centrifuge is rotated at 2800 rpm for 5 minutes. The retention of aqueous liquid by the fibre is measured by weighing the tube and contents after the centrifuging test and comparing this with the weight of the dry tube and dry fibre. Superabsorbent fibre has a retention to centrifuging of at least 10 g/g for 0.9% by weight saline solution.

The superabsorbent polymer is preferably a crosslinked copolymer of 50 to 95% by weight ethylenically unsaturated carboxylic monomer and 5 to 50% by weight copolymerisable ethylenically unsaturated monomer. Superabsorbent fibres and their production are described in EP-A-397410, EP-A-342919, EP-A-269393, EP-A-268498, FR-A-2355929 and WO-A-92/19799. Such fibres are usually formed by extruding an aqueous solution of the copolymer in its non-crosslinked state through a spinneret into a gaseous environment to remove the water to form a fibre or filament and subsequently crosslinking the copolymer, preferably by heating. Preferred carboxylic monomers are methacrylic acid or acrylic acid, but maleic acid and anhydride and iraconic acid are also suitable. Carboxylic monomers may be present in the fibre in free acid and/or water-soluble salt form, suitable salts being formed with ammonia, an amine or an alkali metal. The comonomer preferably comprises an alkyl ester of acrylic or methacrylic acid. The copolymer can be crosslinked by reaction of the carboxylic acid groups either with an external crosslinking agent, such as a polyvalent metal compound to provide ionic crosslinks or a reactive organic group to provide covalent crosslinks, or with pendent reactive groups in the copolymer. The reactive groups can for example be hydroxyl, epoxide, amine or isocyanate groups to form ester, amide or urethane crosslinks respectively. Alternative but less preferred superabsorbent polymers comprise a copolymer of an unsaturated carboxylic monomer such as maleic anhydride with an olefin comonomer such as isobutylene or styrene and a crosslinking agent having hydroxyl or cyclic carbonate groups, as described in U.S. Pat. No. 4,813,945, U.S. Pat. No. 4,743,244, U.S. Pat. No. 4,731,067 and EP-A-301804.

The superabsorbent polymer fibres preferably have a weight of below 30 decitex, most preferably below 20 decitex per filament, for example in the range 2 to 15 decitex per filament. The length of the superabsorbent polymer fibres is generally in the range 1 to 100 mm; staple fibres of length 3 to 12 mm are preferred.

The less absorbent fibres are generally of length in the range 1 to 100 mm. They can for example be short fibres, generally of length 1 to 10 mm, such as cellulosic fibres, for example wood pulp fibres. Other fibres of this length, such as the polyethylene or polypropylene fibrils sold as synthetic pulp, can alternatively or additionally be used, as can cellulose acetate fibrils. Wood pulp fibres may be preferred as the main or only less absorbent fibres when forming nonwoven fabrics for use in disposable personal absorbent products such as diapers, sanitary napkins and incontinence pads.

The less absorbent fibres can alternatively or additionally be textile fibres generally of staple length at least 10 mm and up to 50 or 100 mm. Examples of useful textile fibres are cellulosic fibres such as regenerated cellulose, cotton, cellulose acetate or solvent-spun cellulose fibres, or synthetic fibres such as polyester, polyamide, acrylic, modacrylic, polypropylene, polyethylene, polyvinyl alcohol or polyurethane fibres, or mineral fibres such as glass fibres. In many cases the less absorbent fibres can consist of a mixture of short fibres, for example wood pulp fibres, and textile staple fibres such as polyester or regenerated cellulose fibres. The ratio of short fibres to staple fibres can for example be from 100:1 to 1:2 by weight. The use of textile staple fibres in these proportions generally provides a stronger wet-laid nonwoven fabric.

The overall blend of fibres in the wet-laid nonwoven fabric preferably contains at least 1%, and most preferably at least 5%, for example 5 to 20%, by weight of the superabsorbent polymer fibres. The less absorbent fibres usually form at least 50% by weight of the fibre blend, for example 80 to 95%. The weight ratio of superabsorbent fibres to less absorbent fibres is thus generally 1:100 to 1:1 and is preferably 1:50 to 1:2.

The slurry of superabsorbent polymer fibres and less absorbent fibres can be made in various ways. For example, the superabsorbent polymer fibres and the less absorbent fibres can each be slurried in water and the slurries mixed. Alternatively, the superabsorbent polymer fibres can be slurried in a water-miscible organic liquid in which they do not swell, for example a lower alcohol such as methanol or ethanol, and this slurry can be mixed with (eg added to) a slurry of the less absorbent fibres in water. The superabsorbent polymer fibres can be added as dry fibres to a slurry of the less absorbent fibres in water. Alternatively, the less absorbent fibres can be mixed into an aqueous slurry of the superabsorbent polymer fibres. In a further alternative the superabsorbent polymer fibres and less absorbent fibres can be dry mixed, for example in suspension in air, and then mixed with water to form a slurry. If the less absorbent fibres comprise wood pulp fibres which need to be refined, it is preferred to mix the superabsorbent polymer fibres into the slurry after refining has been completed, as refining will damage the superabsorbent polymer fibres in their water-swollen state.

The slurry can be formed into a nonwoven fabric by any of the techniques known for wet-laying nonwoven fabrics, for example those described in "Manual of Nonwovens" by R. Krcma (4th Edition 1974, Textile Trade Press, Manchester) at pages 222 to 226. In general, the fibres are wet-laid in a process similar to a conventional papermaking process. The fibres are deposited on a foraminous support, generally on a moving mesh screen in a continuous process. The slurry of fibres can be poured at a controlled rate onto a substantially horizontal mesh screen, or the fibres may be deposited on an inclined mesh screen travelling upwards through the slurry. Alternatively, the fibres can be deposited on a mesh screen which is at the surface of a suction drum. The mesh size of the screen should be such as to allow easy drainage of water but to retain the fibres; the most suitable mesh size will generally be in the range 0.2 to 1.5 mm. The mesh can be of metal wire or synthetic polymer, for example polyester filament.

The total fibre content of the slurry as it is deposited on the foraminous support is generally in the range 0.1 to 50 g/liter, preferably 0.1 to 10 g/liter for most types of wet-laying machinery. Much of the water content of the slurry is drained from the deposited fibre layer while it is supported on the mesh screen, preferably with the aid of suction applied below the screen or compression rolls in the later stage of its progress on the mesh screen. The solids content of the wet-laid layer as it is taken off the mesh screen is preferably at least 5% and most preferably at least 10% by weight, and it is generally not more than 30% and usually not more than 20% by weight. The wet-laid layer is then dried, generally by techniques known in papermaking including passage around a heated drum and/or passage between a series of heated rolls. The dry weight of the nonwoven fabric formed is generally at least 25 $g/m^2$ and is usually no more than 2000 $g/m^2$, for example it can be in the range 100 to 500 $g/m^2$.

The wet-laid nonwoven fabric can include dispersed particles such as silica, a zeolite or a mineral clay, such as kaolin or bentonite. Such particles, which preferably are not used at more than 10% by weight of the nonwoven fabric, can be added to the slurry as described in EP-A-437816 or incorporated in the superabsorbent fibres as described in WO-A-92/19799.

The wet-laid nonwoven fabric can be treated with adhesive to increase its cohesive strength and tear resistance. The adhesive can for example be an acrylic polymer, a vinyl acetate polymer or a styrene/butadiene or acrylonitrile/butadiene copolymer. The adhesive can be incorporated in the slurry or sprayed on the fibrous layer as it is being drained or dried.

INDUSTRIAL APPLICABILITY

The absorbent nonwoven fabric of the present invention can be used in absorbent personal products such as tampons, disposable diapers, sanitary napkins or incontinence pads. The fabric can be used as the only absorbent material in such products or can be used with layers of fluffed wood pulp or of cellulosic fibres such as multi-limbed regenerated cellulose fibres.

The absorbent nonwoven fabric can be used in many other applications of the types described in Research Disclosure, January 1992 at pages 60–61, for example in absorbent liners or mats for packaging, disposable wipes, mats, shoe insoles or bed sheets, swellable gaskets or seals, moisture-retention mats in horticulture, moisture-retaining packaging or as a swellable material which prevents ingress of water in underground cables.

The invention is illustrated by the following Examples.

EXAMPLES 1 TO 3

10 decitex superabsorbent fibres of a copolymer of 78 mole % acrylic acid (75% neutralised as sodium salt), 20 mole % methyl acrylate and 2 mole % hexapropylene glycol monomethacrylate were produced by dry spinning from aqueous solution followed by cutting to staple length (6 mm) and crosslinking at 200° C. to form ester crosslinks between the carboxylic acid and hydroxyl groups. The superabsorbent fibres had an absorbency of 50 g/g as measured by the free swell absorbency test and a retention under load of 35 g/g.

The equipment used for preparation of the wet-laid nonwoven fabrics was the standard British Pulp Evaluation Apparatus manufactured by Mavis Manufacturing Company, London. All fabrics were produced as 1.2 g dry weight sheets. The required quantity of dry woodpulp (Rayon XF grade) was dispersed at 5000 revs/min in 2 liters water using a high shear mixer. The wood pulp fibre had an absorbency of less than 10 g/g measured by retention to centrifuging of a 0.9% by weight saline solution. The superabsorbent fibre was dispersed in 100 ml water for a few seconds until it had swollen, and this was added to the dispersed pulp. The mixture was stirred with a spatula. The mixture was then added to the papermaking column, and the paper fabric was formed on a 25 mesh (British Standard Sieve) screen.

The paper fabrics were pressed, and then allowed to dry under ambient conditions, yielding sheets with the following properties.

| | % Superabsorbent Fibres | Wt of Wood Pulp (g) | Wt of Superabsorbent Fibre (g) | Free Swell in 0.9% saline solution (g/g) | Retention under load (g/g) |
| --- | --- | --- | --- | --- | --- |
| Control | 0 | 1.20 | 0 | 9.79 | 8.14 |
| Example 1 | 5 | 1.14 | 0.06 | 10.59 | 9.48 |
| Example 2 | 10 | 1.08 | 0.12 | 11.04 | 10.04 |
| Example 3 | 20 | 0.96 | 0.24 | 12.88 | 10.56 |

Treatment of the paper fabrics with copper II sulphate solution preferentially stains the superabsorbent fibres blue, leaving the woodpulp white. In this way it was possible to observe that the superabsorbent fibres were uniformly distributed through the fabrics.

I claim:

1. A wet-laid nonwoven fabric comprising a blend of 1 to 50% by weight of fibres of weight 2 to 30 decitex per filament and length 3 to 100 mm of a water-swellable water-insoluble superabsorbent polymer, which is a crosslinked copolymer of 50 to 95% by weight ethylenically unsaturated carboxylic monomer and 5 to 50% by weight copolymerisable ethylenically unsaturated monomer, and 99 to 50% by weight of less absorbent fibres having an absorbency of less than 10 g/g measured by retention to centrifuging of a 0.9% by weight saline solution.

2. A fabric according to claim 1, wherein the less absorbent fibres comprise fibres of length 1 to 10 mm.

3. A fabric according to claim 2, wherein the less absorbent fibres comprise wood pulp fibres.

4. A fabric according to claim 2, wherein the less absorbent fibres comprise polypropylene or polyethylene fibrils.

5. A fabric according to claim 1, wherein the less absorbent fibres comprise textile fibres of length 10 to 100 mm.

6. A fabric according to claim 5, wherein the less absorbent fibres of length 10 to 100 mm are cellulosic fibres or polyester, polyamide, acrylic, polypropylene or polyethylene fibres.

7. A fabric according to claim 1, comprising a blend of 5 to 20% by weight of the superabsorbent polymer fibres and 95 to 80% by weight of the less absorbent fibres.

8. A process for the production of a wet-laid nonwoven fabric, in which process fibres having an absorbency of less than 10 g/g, measured by retention to centrifuging of a 0.9% by weight saline solution, are slurried in water, fibers of weight 2 to 30 decitex per filament and length 3 to 100 mm of a water-swellable water-insoluble superabsorbent polymer, which is a crosslinked copolymer of 50 to 95% by weight ethylenically unsaturated carboxylic monomer and 5 to 50% by weight copolymerisable ethylenically unsaturated monomer, are added to this slurry to form a mixed slurry containing both the superabsorbent polymer fibres and the less absorbent fibres, the mixed slurry is deposited as a layer on a foraminous support so that part of the water drains from the layer of slurry on the support, and the resulting fibrous layer is dried to form the nonwoven fabric.

9. A process according to claim 8, wherein the proportion of superabsorbent fibres to less absorbent fibres is from 1:2 to 1:50 by weight.

10. A process according to claim 8, wherein the total fibre content of the slurry as it is deposited on the foraminous support is from 0.1 to 50 grams per liter.

11. A process according to claim 8, wherein the superabsorbent polymer fibres are slurried in a water-miscible organic liquid in which they do not swell and the resulting slurry is mixed with a slurry of the less absorbent fibres in water.

12. A process according to claim 8, wherein the superabsorbent polymer fibres are added as dry fibres to a slurry of the less absorbent fibres in water.

* * * * *